United States Patent
Klusener et al.

(10) Patent No.: US 9,758,443 B2
(45) Date of Patent: Sep. 12, 2017

(54) SOLIDS CONTENT CONTROL IN IONIC LIQUID ALKYLATION PROCESS

(71) Applicants: SHELL OIL COMPANY, Houston, TX (US); CHINA UNIVERSITY OF PETROLEUM, Beijung (CN)

(72) Inventors: Peter Anton August Klusener, Amsterdam (NL); Rui Zhang, Beijing (CN)

(73) Assignee: SHELL OIL COMPANY, Houston, TX (US)

( * ) Notice: Subject to any disclaimer, the term of this patent is extended or adjusted under 35 U.S.C. 154(b) by 0 days.

(21) Appl. No.: 14/651,329

(22) PCT Filed: Dec. 13, 2013

(86) PCT No.: PCT/EP2013/076610
§ 371 (c)(1),
(2) Date: Jun. 11, 2015

(87) PCT Pub. No.: WO2014/091016
PCT Pub. Date: Jun. 19, 2014

(65) Prior Publication Data
US 2015/0315094 A1    Nov. 5, 2015

(30) Foreign Application Priority Data
Dec. 14, 2012  (WO) ............... PCT/CN2012/086617

(51) Int. Cl.
*C07C 2/56* (2006.01)
*C07C 2/62* (2006.01)
(Continued)

(52) U.S. Cl.
CPC .............. *C07C 2/58* (2013.01); *C10G 29/205* (2013.01); *C07C 2531/02* (2013.01)

(58) Field of Classification Search
CPC ................ C07C 2/56; C07C 2/59; C07C 2/62
(Continued)

(56) References Cited

U.S. PATENT DOCUMENTS

| 7,285,698 | B2 | 10/2007 | Liu et al. |
| 2004/0133056 | A1 | 7/2004 | Liu et al. |
| 2010/0130799 | A1* | 5/2010 | Ahmed ................ B01J 31/0277 585/311 |

FOREIGN PATENT DOCUMENTS

| WO | 2010062902 | 6/2010 |
| WO | 2011015639 | 2/2011 |

OTHER PUBLICATIONS

PCT International Search Report and Written Opinion dated Feb. 10, 2014 of PCT/EP2013/076610 filed Dec. 13, 2013.
(Continued)

*Primary Examiner* — Thuan D Dang

(57) ABSTRACT

The present invention relates to a continuous or non-continuous ionic liquid alkylation process comprising a step for solids removal, the process further comprising the steps (a) measuring the solids content in the ionic liquid alkylation process stream by on line (in situ) or off line sampling; (b) in response to the solids measurement signal, regulating the flow of the ionic liquid side stream to be sent to the solids removal device; (c) regulating the flow of the fresh ionic liquid inlet stream, for controlling the solids content in the ionic liquid alkylation process to a pre-defined level. The process of the invention provides a means to more efficiently run an ionic liquid alkylation process.

8 Claims, 2 Drawing Sheets

(51) Int. Cl.
*C07C 2/58* (2006.01)
*C10G 29/20* (2006.01)

(58) Field of Classification Search
USPC .............. 585/710, 722, 727, 728, 904, 956
See application file for complete search history.

(56) References Cited

OTHER PUBLICATIONS

EP Communication under Rule 71(3)EPC dated May 10, 2016.
Letter to EPO with reference to the Communication pursuant to Rules 161(1) and (2) EPC dated Jul. 31, 2015 together with amendments made to the claims.
Albright, L.F.; "Present & Future Alkylation Processes in Refineries", American Chemical Society, Ind. Eng. Res, vol. 48, No. 3; pp. 1409-1413; 2009.
Corma, Avelino, et al.; "Chemistry, Catalysts, and Processes for Isoparaffin-Olefin Alkylations Actual Situation & Future Trends"; Catalysis Reviews: Science & Engineering, vol. 35; No. 4, pp. 483-570, 1993.
Liu, et al.; "Ionic Liquid Alkylation Process Produces High-Quality Gasoline"; Oil & Gas Journal.; vol. 104, No. 40; pp. 52-56; 2006.

\* cited by examiner

SOLIDS CONTENT CONTROL IN IONIC LIQUID ALKYLATION PROCESS

PRIORITY CLAIM

The present application is the National Stage (§371) of International Application No. PCT/EP2013/076610, filed Dec. 13, 2013, which claims priority from International Application No. PCT/CN2012/086617, filed Dec. 14, 2012 incorporated herein by reference.

FIELD OF THE INVENTION

The present invention provides a means and a process for controlling the solids content in an ionic liquid alkylation process.

BACKGROUND OF THE INVENTION

Recently, new ionic liquid alkylation processes have been disclosed for the production of alkylates, in particular fuel-blending components like trimethylpentanes (TMPs), which have research octane numbers (RONs) of greater than 100. In such processes isoparaffins are alkylated with olefins using an acidic ionic liquid catalyst.

For instance, U.S. Pat. No. 7,285,698 discloses a process in which a composite ionic liquid catalyst is used to react isobutane with a butane under alkylation conditions. The reactor effluent is separated and the ionic liquid phase is recycled to the reactor while the hydrocarbon phase is treated to retrieve the alkylate. It has however been found that during operation of such an ionic liquid alkylation process, solids are formed. As the reaction progresses, these solids accumulate in the reaction zone and may lead to blockage of pathways and/or valves. In WO2011/015639 a process is described for removal of the solids formed during the ionic liquid alkylation process.

Figure 1:
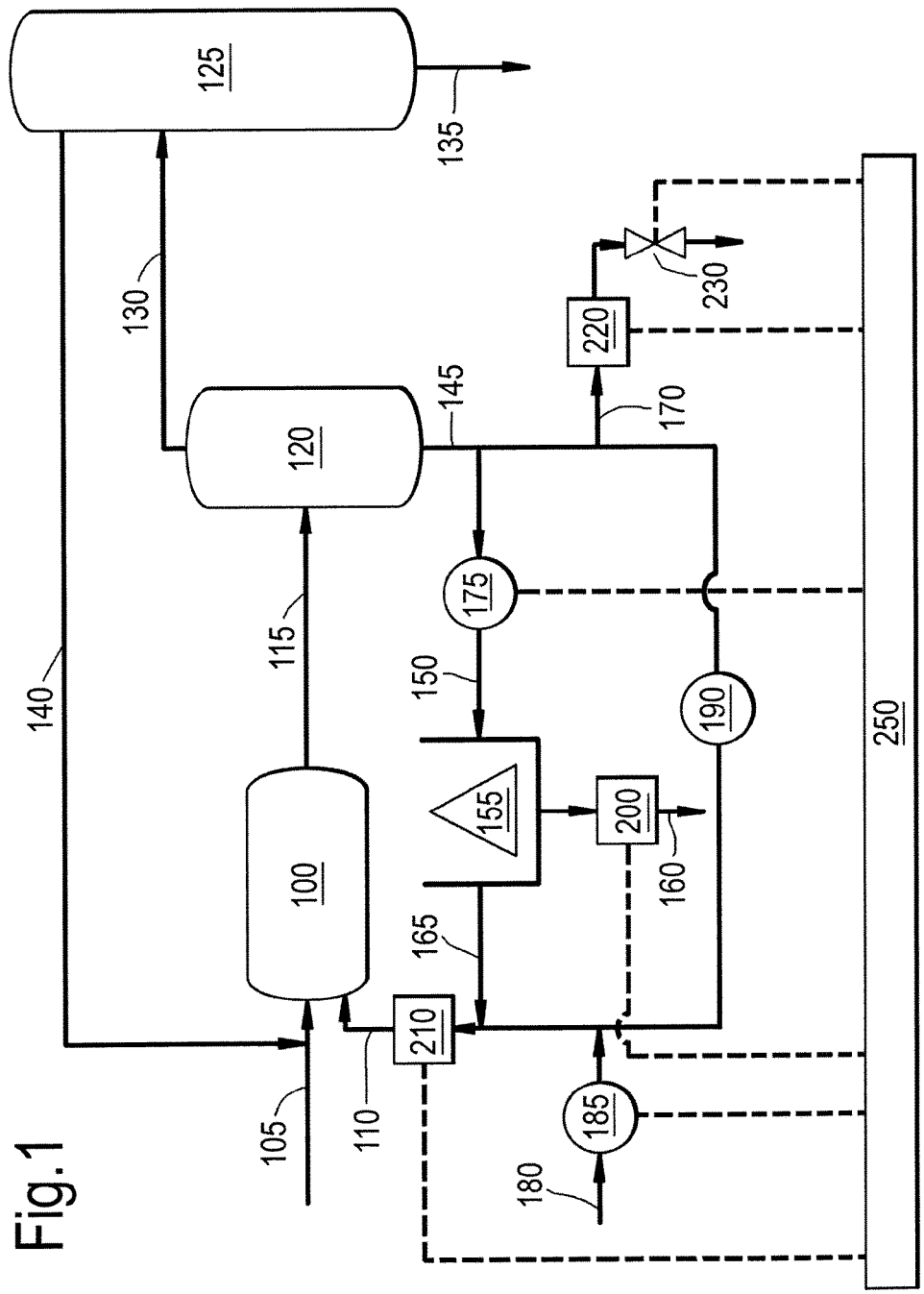
FIG. 1 is a schematic representation of a process according to the invention.

It is important to maintain the solids content in the ionic alkylation process at pre-defined levels thereby minimizing the need for addition of fresh ionic liquid catalyst.

SUMMARY OF THE INVENTION

It has been found that the solids content in an ionic liquid alkylation process can be followed by measuring the solids content in the ionic liquid alkylation process stream by on line (in situ) or off line sampling.

Accordingly, the present invention provides a continuous or non-continuous ionic liquid alkylation process comprising a step for solids removal, the process further comprising the steps
(a) measuring the solids content in the ionic liquid alkylation process stream by on line (in situ) or off line sampling;
(b) in response to the solids measurement signal, regulating the flow of the ionic liquid side stream to be sent to the solids removal device;
(c) regulating the flow of the fresh ionic liquid inlet stream, for controlling the solids content in the ionic liquid alkylation process to a pre-defined level.

Particularly useful is a continuous alkylation process wherein Focused Beam Reflectance Measurement (FRBM®) technology is used for on line measurement of solids content in step (a).

By controlling the solids content in the process streams, the process is more efficient, requires less materials and produces higher yields.

DETAILED DESCRIPTION OF THE INVENTION

The solids, the content of which is measured according to the process of this invention, are formed in a process wherein an alkylate is prepared by reacting an isoparaffin with an olefin, in particular isobutane and a butene. The obtained alkylate is particularly suitable for gasoline blending purposes or for use in aviation gasoline production. In the alkylation process, the isoparaffin and the olefin are provided to a reaction zone. In the reaction zone a hydrocarbon mixture comprising isoparaffin and olefin is contacted with a catalyst suitable for alkylation. The hydrocarbon mixture comprises olefin typically supplied externally, i.e. fresh olefin, and comprises isoparaffin. The isoparaffin may be externally supplied isoparaffin, i.e. fresh isoparaffin, and/or isoparaffin which is recycled from any other part of the process. The (fresh) isoparaffin and olefin may be supplied to the process separately, however typically the (fresh) isoparaffin and the (fresh) olefin are provided to the reaction zone as a mixture comprising isoparaffin and olefin.

In the present alkylation process the catalyst is a composite mixture comprising the ionic liquid (herein below also referred to a catalyst). Ionic liquids are known in the art for their ability to catalyse alkylation reactions. The catalyst used in the present alkylation process is a composite ionic liquid comprising ammonium cations and anions which are composite coordinate anions derived from two or more metal salts. In particular, the cations are derived from a hydrohalide of an alkyl-containing amine, imidazolium or pyridine. Preferably, the cations comprise cations of ammonium salts, for example nitrogen atoms, which are saturated with four substituents, among which there is at least one hydrogen atom and one alkyl group. More preferably, the alkyl substituent is at least one selected from methyl, ethyl, propyl, butyl, amyl, and hexyl groups. Examples of preferred ammonium cations include triethylammonium (NEt$_3$H$^+$) and methyldiethyl-ammonium cations (MeNEt$_2$H$^+$), cations in which the nitrogen is part of a cyclic structure (e.g. like in piperidine and pyrrolidine) or

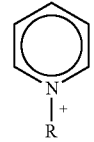

The anions of the composite ionic liquid are preferably derived from aluminium based Lewis acids, in particular aluminium halides, preferably aluminium (III) chloride. Due the high acidity of the aluminium chloride Lewis acid it is preferred to combine the aluminium chloride, or other aluminium halide, with a second or more metal halide, sulfate or nitrate to form a coordinate anion, in particular a coordinate anion derived from two or more metal halides, wherein at least one metal halide is an aluminium halide. Suitable further metal halides, sulfates or nitrates, may be selected from halides, sulfates or nitrates of metals selected from the group consisting of Group IB elements of the Periodic Table, Group IIB elements of the Periodic Table and transition elements of the Periodic Table. Preferred metals include copper, iron, zinc, nickel, cobalt, molybdenum, silver or platinum. Preferably, the metal halides, sulfates or nitrates, are metal halides, more preferably chlorides or bromides, such as copper (I) chloride, copper (II) chloride, nickel (II) chloride, iron (II) chloride. Preferably, the molar ratio of the aluminium compound to the other metal compounds in the range of from 1:100-100:1, more preferably of from 1:1-100:1, or even more preferably of from 2:1-30:1. By using a coordinate anion comprising aluminium and another metal, an improved alkylate product may be obtained. A method for preparing such catalyst is for instance described in U.S. Pat. No. 7,285,698. Particularly preferred catalysts are acidic ionic liquid catalysts comprising a coordinate anion derived from aluminium(III) chloride and copper(II) chloride or aluminium(III) chloride and copper(I) chloride.

As mentioned herein above, the hydrocarbon mixture comprising isoparaffin and olefin is contacted with the catalyst in the reaction zone. The hydrocarbon mixture is mixed in the reaction zone with the catalyst to form a reaction mixture. As the reaction progresses the reaction mixture will, besides hydrocarbon reactants and acidic ionic liquid, additionally comprise products. Mixing of the hydrocarbon mixture and the catalyst may be done by any suitable means for mixing two or more liquids, including dynamic and static mixers. In contact with the catalyst, the isoparaffins and olefins react under alkylation conditions to form an alkylate.

The formed alkylate is obtained from the reaction zone in the form of an alkylate-comprising effluent. The alkylate-comprising effluent still comprises a substantial amount of unreacted isoparaffin. Therefore, part of the alkylate-comprising effluent may be recycled to the reaction zone to maintain a high ratio of isoparaffin to olefin in hydrocarbon mixture in the reaction zone.

At least part of the alkylate-comprising effluent of the reaction zone is separated in a separator unit into a hydrocarbon-rich phase and an ionic liquid catalyst-rich phase. At least part of the hydrocarbon-rich phase is treated and/or fractionated (e.g. by distillation) to retrieve the alkylate and optionally other components in the hydrocarbon phase, such as unreacted isoparaffin or n-paraffins. Preferably, such isoparaffin is at least partly reused to form part of the isoparaffin feed provided to the process. This may be done by recycling at least part of the isoparaffin, or a stream comprising isoparaffin obtained from the fractionation of the hydrocarbon-rich phase, and combining it with the isoparaffin feed to the process.

Reference herein to a hydrocarbon-rich phase is to a phase comprising more than 50 mol % of hydrocarbons, based on the total moles of hydrocarbon and ionic liquid catalyst.

Reference herein to an ionic liquid catalyst-rich phase is to a phase comprising more than 50 mol % of ionic liquid catalyst, based on the total moles of hydrocarbon and ionic liquid catalyst.

Due to the low affinity of the ionic liquid for hydrocarbons and the difference in density between the hydrocarbons and the ionic liquid catalyst, the separation between the two phases is suitably done using for example well known settler means, wherein the hydrocarbons and catalyst separate into an upper predominantly hydrocarbon phase and lower predominantly catalyst phase or by using any other suitable liquid/liquid separator. Such liquid/liquid separators are known to the skilled person and include cyclone and centrifugal separators. The catalyst phase is generally recycled back to the reactor.

As described herein before, during the alkylation reaction solids are formed in the reaction zone. Reference herein to solids is to non-dissolved solid particles. The solids predominantly consist out of metals, metal compounds and/or metal salts which were originally comprised in the composite ionic liquid catalyst. Preferably, the solids comprise at least 10 wt % metal, i.e. either in metallic, covalently bound or ionic form, based the total weight of the solids, wherein the metal is a metal that was introduced to the process as part of the acidic ionic liquid catalyst. The solids may also comprise contaminant components, which were introduced into the reaction mixture as contaminants in the hydrocarbon mixture or the composite ionic liquid. Alternatively, the solids may be the product of a chemical reaction involving any of the above-mentioned compounds.

The solids may have any size, however the solids typically have an average size of in the range of from 0.1 to 10 µm. In particular, at least 50% of the solids have a particle size below 5 µm, more particular 80% of the solids have a particle size below 5 µm based on the total number of solid particles.

In WO2011015639 it is described that although during mixing these solids are dispersed throughout the reaction mixture, upon separation of the alkylate-comprising effluent it was found that the solids, to a large extent, accumulate in the composite ionic liquid catalyst-rich phase. If the catalyst-rich phase is subsequently recycled to the reaction zone to become part of the reaction mixture in the reaction zone, the solids accumulate in the reaction zone, resulting in undesirably high solids content in the reaction zone. A high solids content in the reaction zone may for instance result in blockage of pathways or valves in the reactor zone and pipes to and from the separation unit, due to precipitation of solids. In addition, at high solids content the solids may agglomerate to form large aggregates, resulting in increased blockage risk. Therefore, (at least part of) the solids are removed from the reaction zone. It is not required to remove all solids from the reaction zone. Preferably, solids are removed from the reaction zone to an extent that the reaction mixture (i.e. a mixture comprising hydrocarbon reactants, composite ionic liquid and products) comprises in the range of from 0.05 to 5 wt %, more preferably at most 2 wt % of solids, based on the total weight composite ionic liquid in the reaction zone.

The solids may be removed from the reaction zone by withdrawing at least part of the reaction mixture from the reaction zone as a solids-comprising effluent. This solids-comprising effluent comprises next to the solid also hydrocarbons and composite ionic liquid, wherein the hydrocarbons typically include isoparaffins and alkylate. Subsequently, (at least part of) the solids in at least part of the solids-comprising effluent are removed. After the removal of solids a solids-depleted effluent is obtained. Preferably, at least part of the solids-depleted effluent is recycled to the reactor for efficient use of the materials.

The solids-comprising effluent is first separated in a typical separator unit into a catalyst-rich phase and a hydrocarbon-rich phase and the solids are subsequently removed from the catalyst-rich phase. Subsequently, the solids-depleted catalyst can be reintroduced into the reaction zone.

The solids may be removed by any suitable means for removing solids from liquids, including but not limited to filtration, precipitation (e.g. in a settler unit) and centrifugation processes, and processes using a cyclone. Such processes are well known in the art. In view of process efficiency, centrifugation is the preferred process for removing the solids from the catalyst-rich phase.

Due to the specific nature of ionic liquids it is preferred that the removal of the solids is performed at such a temperature that the acidic ionic liquid catalyst is liquid. In particular, it is preferred to remove the solids at a temperature in the range of from 5 to 80° C., more preferably of from 20 to 60° C., while ensuring that the temperature is such that the ionic liquid remains a liquid. By removing the solids at elevated temperatures, the viscosity of the ionic liquid is lower while the density is reduced, which may be beneficial in view of decreased time and power input required to obtained separation of the solids from the liquid.

The solids may be removed from the process in any form, however typically the solids are removed in the form of a paste of solids. Such a paste may comprise next to solid particles for instance some residual ionic liquid and/or hydrocarbons (which may be for instance some polymeric material formed as side product during the reaction). Depending on the amount of residual ionic liquid, the solids may also be removed from the process in the form of a slurry. In this text, the term "paste" is meant to also refer to "slurry". Typically, a paste contains at least 30% of solid particles.

According to an embodiment of the invention, the signal produced by the device measuring the solids content, preferably a Focused Beam Reflectance Measurement (FRBM®) device, controls the pump that regulates the flow of the ionic liquid side stream to be sent to the solids removal device.

Preferably, the solids content is measured by the measuring device in the inlet line for introducing ionic liquid into the reaction zone.

In a further embodiment, through the inlet line a combined stream of fresh and recycled ionic liquid is introduced into the reaction zone.

In an embodiment of the invention, the signal produced by the device measuring the solids content, preferably a Focused Beam Reflectance Measurement device, controls the pump that pumps fresh ionic liquid into the system. Introduction of fresh ionic liquid to make up for loss of ionic liquid in the process, e.g. due to solid formation and bleed.

In a further embodiment of the invention, the signal produced by the device measuring the solids content, preferably a Focused Beam Reflectance Measurement device, controls a valve that controls the flow of spent ionic liquid bleed. This bleed is necessary to balance with the introduction of fresh ionic liquid into the system.

In the alkylation process, an isoparaffin and an olefin are reacted to form an alkylate by contacting the hydrocarbon mixture comprising isoparaffin and olefin with the catalyst under alkylation conditions. Preferably, the hydrocarbon mixture comprises at least isobutane and optionally isopentane, or a mixture thereof, as an isoparaffin. The hydrocarbon mixture preferably comprises at least an olefin comprising in the range of from 2 to 8 carbon atoms, more preferably of from 3 to 6 carbon atoms, even more preferably 4 or 5 carbon atoms. Examples of suitable olefins include, propene, 1-butene, 2-butene, isobutene, 1-pentene, 2-pentene, 2-methyl-1-butene, 3-methyl-1-butene, 2-methyl-2-butene.

Isoparaffins and olefins are supplied to the process in a molar ratio, which is preferably 1 or higher, and typically in the range of from 1:1 to 40:1, more preferably 1:1 to 20:1. In the case of a continuous process, excess isoparaffin can be recycled for reuse in the hydrocarbon mixture.

The alkylation conditions (or process conditions) are those known in the art for this type of alkylation processes. Actual operational process conditions are for example dependent of the exact composition of the hydrocarbon mixture and catalyst, and the like.

The temperature in the alkylation reactor is preferably in the range of from −20 to 100° C., more preferably in the range of from 0 to 50° C. In any case the temperature must be high enough to ensure that the ionic liquid catalyst is in the liquid state.

To suppress vapour formation in the reactor, the process may be performed under pressure; preferably the pressure in the reactor is in the range of from 0.1 to 1.6 MPa.

Preferably, the composite ionic liquid catalyst to hydrocarbon ratio in the alkylation reaction zone is at least 0.5, preferably 0.9 more preferably at least 1. Preferably, the composite ionic liquid catalyst to hydrocarbon ratio in the reaction zone is in the range of from 1 to 10.

The hydrocarbon mixture may be contacted with the catalyst in any suitable alkylation reactor. This may be done in a batch-wise, a semi-continuous or continuous process. Reactors such as used in liquid acid catalysed alkylation can be used (see L. F. Albright, Ind. Eng. Res. (2009) 1409 and A. Corma and A. Martinez, Catal. Rev. 35 (1993) 483); alternatively the reactor is a loop reactor, optionally with multiple injection points for the hydrocarbon feed, optionally equipped with static mixers to ensure good contact between the hydrocarbon mixture and catalyst, optionally with cooling in between the injection points, optionally by applying cooling via partial vaporization of volatile hydrocarbon components (see Catal. Rev. 35 (1993) 483), optionally with an outlet outside the reaction zone (see WO2011/015639). In the prior art diagrams are available of alkylation process line-ups which are suitable for application in the process of this invention, e.g. in U.S. Pat. No. 7,285,698, Oil & Gas J., vol 104 (40) (2006) p 52-56 and Catal. Rev. 35 (1993) 483.

DESCRIPTION OF THE DRAWINGS

In FIG. 1 a schematic representation is given of a process according to the invention.

A mixture, comprising olefin and isoparaffin is provided to reactor 100 through line 105. Also ionic liquid catalyst is provided to reaction zone 100, through inlet line 110. In reaction zone 100, the hydrocarbon mixture and catalyst are mixed under alkylation conditions. Through line 115, a solids-comprising effluent comprising hydrocarbons and acidic ionic liquid is withdrawn from the reaction zone. Part of this effluent may be directly recycled to the reactor or combined with line 105 via a recycle line (not shown). At least part of the effluent is supplied to liquid/liquid separation unit 120, e.g. a settler unit. In liquid/liquid separation unit 120, a hydrocarbon-rich phase and catalyst-rich phase separate under influence of gravity or centrifugal forces. Part of the hydrocarbon-rich phase may be directly recycled to the reactor or combined with line 105 via a recycle line (not shown). At least part of the hydrocarbon-rich phase is provided to fractionator 125 through line 130. From the bottom of fractionator 125, an alkylate-comprising product is retrieved through line 135. The alkylate-comprising product can be used for instance for fuel blending purposes. Additionally, an isoparaffin-comprising stream is retrieved from fractionator 125, which is recycled via line 140 to become part of the mixture in line 105. Other hydrocarbon-comprising streams (not shown) may also be retrieved from fractionator 125.

The ionic liquid catalyst phase, containing solids, can be recycled via line 145 to reactor 100. Part or all of the catalyst can be diverted from line 145 via pump 175 by line 150 to centrifuge 155. In centrifuge 155, solids are removed from the ionic liquid catalyst phase under influence of the centrifugal forces, and are retrieved through a flow meter of solids concentrate 200 and further via line 160. The remaining acidic ionic liquid catalyst phase exits centrifuge 155 via line 165. Optionally, hydrochloride gas is provided to the ionic liquid catalyst phase in line 165 (not shown) for which optionally a mixing device (not shown), e.g. a venturi absorber, is used to mix the hydrogen chloride gas into the ionic liquid.

A Focused Beam Reflectance Measurement (FRBM®) device 210 is located in the process stream at a position downstream in the line after the point where lines 165 and 145 come together. The FRBM® device measures the solids content in ionic liquid feed line 110. Through line 145 the remainder of the ionic liquid catalyst phase is pumped, via recycle pump 190, and in addition fresh ionic liquid catalyst may be introduced into line 145 via line 180, through pump 185.

The FRBM® device 210 sends via computer control system 250 a control signal to the pump 175 controlling the flow to the centrifuge 155. The centrifuge produces a slurry or paste containing solids and liquid, the flow of the slurry or paste being dependent on both the pump rate of pump 175 and the solids content of the feed to the centrifuge 155. The computer control system 250 sends a control signal to the pump 185 which pumps fresh ionic liquid into the system. Also the materials balance is controlled by computer control system 250, which sends a signal to valve 230 to control spent ionic liquid bleed flow. Optionally also a level control meter in liquid/liquid separation unit 120 sends a signal to the computer control system 250 to adjust the feed of fresh ionic liquid by pump 185 or the bleed of spent ionic liquid by control valve 230. The spent ionic liquid flows through line 170 and is measured by flow meter 220.

The (partially recycled) ionic liquid catalyst phase is subsequently directed back to reaction zone 100. Computer control system 250 can be controlled automatically or manually.

The invention is illustrated by the following examples.

EXAMPLES

An FMBR apparatus from Mettler Toledo was used. The cord length determined with FBRM is a measure for the particle size.

Ionic liquid was prepared according to the procedures described in U.S. Pat. No. 7,285,698.

Examples 1-3

Figure 2:
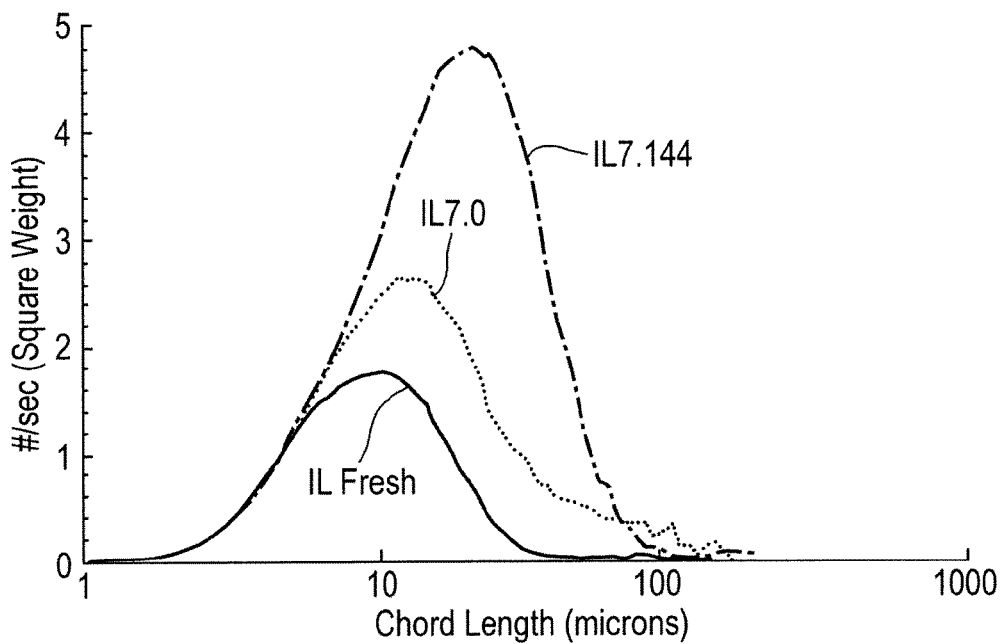
FIG. 2 depicts the FBRM results for Examples 1-3.

The graph in FIG. 2 shows three FBRM graphs.
Example 1) shows fresh ionic liquid.
Example 2) shows a mixture of fresh and reused ionic liquid.
Example 3) shows the ionic liquid from example 2 after 144 h runtime in an alkylation process according to U.S. Pat. No. 7,285,698.
The graphs indicate that solids content as well as the particle size increases as function of runtime. In examples 1 and 2 the solids were isolated and the solids fraction was 0.5 and 1.5 w %, respectively.

Example 4

Figure 3:
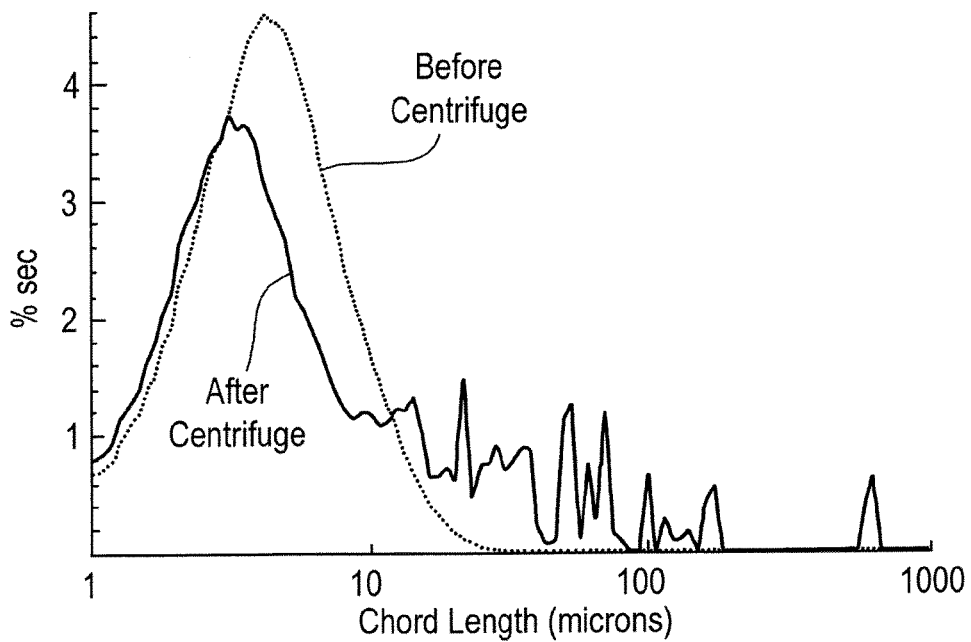
FIG. 3 depicts the FBRM results for Examples 4-5.

The graph of FIG. 3 shows the FBRM curve of a non-centrifuged ionic liquid sample (example 4), taken from an alkylation process according to U.S. Pat. No. 7,285,698. Example 5 shows the FBRM curve of the sample ex example 4 after centrifuge and solids removal, also in FIG. 3. The spikes in example 5 for cord lengths above 10 microns are artefacts as ingress of air bubbles occurred during the measurement due to the small sample size and can be ignored.

These examples show that FBRM can be used to measure solids content as well as particle size. FBRM apparatus is commercially available and can be applied for in situ measurement. The application of FBRM is just one example of in situ solids measurement. Any method a known by those skilled in the art to be applied on line (in situ) or off line sampling and analysis is part of the invention.

That which is claimed is:

1. A continuous or non-continuous ionic liquid alkylation process comprising a step for solids removal, the process further comprising the steps of:
   (a) measuring with a measuring device the solids content in the ionic liquid alkylation process stream by on line (in situ) or off line sampling;
   (b) in response to the solids measurement signal, regulating the flow of an ionic liquid side stream to be sent to the solids removal device wherein the solids content is maintained at a pre-defined level in the range of from 0.05 to 5 wt % solids based on the total weight of composite ionic liquid in the reaction zone;
   (c) regulating the flow of a fresh ionic liquid inlet stream, for controlling the solids content in the ionic liquid alkylation process to the pre-defined level.

2. The process according to claim 1, wherein the process is a continuous process and wherein Focused Beam Reflectance Measurement (FRBM®) technology is used for on line measurement of solids content in step (a).

3. The process according to claim 1, wherein the solids content is measured in the inlet line for introducing ionic liquid into the reaction zone.

4. The process according to claim 3, wherein through the inlet line a combined stream of fresh and recycled ionic liquid is introduced into the reaction zone.

5. The process according to claim 1, wherein the signal produced by the device measuring the solids content controls a pump that regulates the flow of the ionic liquid side stream to be sent to the solids removal device.

6. The process according to claim 1, wherein the signal produced by the device measuring the solids content controls a pump that pumps fresh ionic liquid into the system.

7. The process according to claim 1, wherein the signal produced by the device measuring the solids content controls a valve that controls the flow of spent ionic liquid bleed.

8. The process of claim 1, wherein the ionic liquid is a composite ionic liquid comprising ammonium cations and anions being composite coordinate anions derived from two or more metal salts.

* * * * *